(12) United States Patent
Senegas et al.

(10) Patent No.: US 12,042,306 B2
(45) Date of Patent: Jul. 23, 2024

(54) CARDIAC MOTION SIGNAL DERIVED FROM OPTICAL IMAGES

(71) Applicant: KONINKLIJKE PHILIPS N.V., Eindhoven (NL)

(72) Inventors: Julien Senegas, Hamburg (DE); Sascha Krueger, Hamburg (DE); Daniel Wirtz, Hamburg (DE); Christian Stehning, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 500 days.

(21) Appl. No.: 16/492,643

(22) PCT Filed: Mar. 16, 2018

(86) PCT No.: PCT/EP2018/056672
§ 371 (c)(1),
(2) Date: Sep. 10, 2019

(87) PCT Pub. No.: WO2018/167275
PCT Pub. Date: Sep. 20, 2018

(65) Prior Publication Data
US 2020/0046300 A1 Feb. 13, 2020

(30) Foreign Application Priority Data
Mar. 17, 2017 (EP) .................................... 17161481

(51) Int. Cl.
*A61B 5/00* (2006.01)
*A61B 5/024* (2006.01)
(Continued)

(52) U.S. Cl.
CPC .......... *A61B 5/7292* (2013.01); *A61B 5/0077* (2013.01); *A61B 5/02438* (2013.01);
(Continued)

(58) Field of Classification Search
CPC . A61B 5/7292; A61B 5/0077; A61B 5/02438; A61B 5/055; A61B 5/1102;
(Continued)

(56) References Cited

U.S. PATENT DOCUMENTS

| 6,937,696 | B1 * | 8/2005 | Mostafavi | ................ | H05G 1/10 |
| | | | | | 378/95 |
| 9,121,918 | B2 | 9/2015 | Hirata | | |

(Continued)

OTHER PUBLICATIONS

McLaren et al. 2015 Magn. Reson. Med. 74:571-577 (Year: 2015).*
(Continued)

*Primary Examiner* — Keith M Raymond
*Assistant Examiner* — Patrick M Mehl

(57) ABSTRACT

The invention provides for a medical apparatus (100, 200, 300, 500) comprising an optical imaging system (106) configured for acquiring a series of optical images (544) descriptive of cardiac motion of a subject (102). The medical apparatus further comprises a memory (534) for storing machine executable instructions (540). The medical apparatus further comprises a processor (530) for controlling the medical apparatus. Execution of the machine executable instructions causes the processor to repeatedly: acquire (400) a series of images using the optical imaging system, wherein the series of images are acquired at a rate of at least 10 frames per second; and derive (402) a cardiac motion signal (546) from the series of images, wherein the cardiac motion signal is derived by tracking motion of at least a group of pixels within the series of images.

18 Claims, 8 Drawing Sheets

(51) Int. Cl.
| | |
|---|---|
| A61B 5/055 | (2006.01) |
| A61B 5/11 | (2006.01) |
| A61B 6/00 | (2024.01) |
| A61B 6/03 | (2006.01) |
| A61B 8/00 | (2006.01) |
| G01R 33/567 | (2006.01) |
| G06T 7/00 | (2017.01) |
| G06T 7/20 | (2017.01) |

(52) U.S. Cl.
CPC ............ *A61B 5/055* (2013.01); *A61B 5/1102* (2013.01); *A61B 5/1128* (2013.01); *A61B 5/6823* (2013.01); *A61B 5/7425* (2013.01); *A61B 6/032* (2013.01); *A61B 6/037* (2013.01); *A61B 6/541* (2013.01); *A61B 8/543* (2013.01); *G01R 33/5673* (2013.01); *G06T 7/0016* (2013.01); *G06T 7/20* (2013.01); *G06T 7/97* (2017.01); *G06T 2207/10016* (2013.01); *G06T 2207/10088* (2013.01); *G06T 2207/30076* (2013.01)

(58) Field of Classification Search
CPC ... A61B 5/1128; A61B 5/6823; A61B 5/7425; A61B 6/032; A61B 6/037; A61B 6/541; A61B 8/543; A61B 8/5284; A61B 8/00; G01R 33/5673; G06T 7/0016; G06T 7/20; G06T 7/97; G06T 2207/10016; G06T 2207/10088; G06T 2207/30076
See application file for complete search history.

(56) References Cited

U.S. PATENT DOCUMENTS

| | | |
|---|---|---|
| 2004/0116804 A1 | 6/2004 | Mostafavi |
| 2010/0061596 A1 | 3/2010 | Mostafavi et al. |
| 2010/0217139 A1 | 8/2010 | Pinter et al. |
| 2012/0253178 A1 | 10/2012 | Mostafavi |
| 2013/0274590 A1 | 10/2013 | Auboiroux et al. |
| 2014/0023236 A1 | 1/2014 | Jeanne et al. |
| 2016/0073962 A1 | 3/2016 | Yu et al. |
| 2016/0331239 A1 | 11/2016 | Maclaren et al. |

OTHER PUBLICATIONS

Ren et al. 2017 IEEE Trans. Microwave Theory Techniques 65:3519-3529 (Year: 2017).*
Hu et al. 2009 Ann. Int. Conf. IEEE Eng. Med. Biol. Soc. 6550-6553 (Year: 2009).*
MacLaren et al. 2012 Plos One 7:e48088 9pages (Year: 2012).*
Wikipedia 2016; "Magnification" internet address https://web.archive.org/web/20161013114648/https://en.wikipedia.org/wiki/Magnification 5 pages (Year: 2016).*
Weinhandl et al. 2010 J. Biomech. 43:1437-1440 (Year: 2010).*
Brahme et al. 2008 Med. Phys. 35:1670-1681 (Year: 2008).*
Yang et al. 2017 IEEE Trans. Multimedia 19:1625-1636 (Year: 2017).*
Prochazka et al. 2016 Sensors 16 pub. 996 11 pages (Year: 2016).*
Saeed et al. 2010 LNCS LNIP 6169 11-22 (Year: 2010).*
Spicher et al. 2016 BioMed. Eng. OnLine 15 126 28 pages (Year: 2016).*
Cai et al. 2017 Multimed. Tools Appl. 76:4313-4355 (Year: 2016).*
Da Costa 1995 Optics Communications 117:395-398 (Year: 1995).*
Olesen 2011 PhD Thesis Technical University of Denmark No. 266 (Year: 2011).*
MacLarren et al "Contact-Free Physiological Monitoring Using a Markerless Optical System" Magnetic Reson. in Med. 74.2 (2015) p. 571-577.
Verkruysse W, et al "Remote Plethysmographic Imaging Using Ambient Light". Opt Express 2008;16:21434-21445.
Scully CG, et al "Physiological Parameter Monitoring from Optical Recordings with a Mobile Phone" IEEE Trans Biomed Eng 2012;59:303-306.
Pinheiro E, et al "Theory and Developments in an Unobtrusive Cardiovascular System Representation: Ballistocardiography" The Open Biomedical Engineering Journal, 2010, 4, 201-216.
Joel Schaerer et al., "Multi-dimensional respiratory motion tracking from markerless optical surface imaging based on deformable mesh registration" Phys. Med. Biol. 57 (2012) 357-373.
Lei Qin et al., "Prospective Head-Movement Correction for High-Resolution MRI Using an In-Bore Optical Tracking System" Magn Reson Med. Oct. 2009 ; 62(4): 924-934. doi: 10.1002/mrm.22076.
International Search Report from PCT/EP2018/056672 dated Jun. 7, 2018.

* cited by examiner

CARDIAC MOTION SIGNAL DERIVED FROM OPTICAL IMAGES

CROSS REFERENCE TO RELATED APPLICATIONS

This application is a U.S. national phase application of International Application No. PCT/EP2018/056672 filed on Mar. 16, 2018, which claims the benefit of EP Application Serial No. 17161481.1 filed on Mar. 17, 2017 and is incorporated herein by reference.

FIELD OF THE INVENTION

The invention relates to the monitoring of cardiac signals, in particular the monitoring of cardiac signals for gated acquisition of medical imaging data.

BACKGROUND OF THE INVENTION

Cardiac signals can be monitored using an electrocardiogram (ECG) or a photoplethysmogram (PPG) signal. Such signals can also be used to gate the acquisition of medical imaging data either to mitigate the effect of heart motion or to capture images which are resolved relative to the motion phase of the heart.

The journal article Maclaren et. al., "Contact-free physiological monitoring using a markerless optical system." *Magnetic resonance in medicine* 74.2 (2015): 571-577 discloses an MR-compatible camera was mounted on an eight-channel head coil. Video data of the skin was processed offline to derive cardiac and respiratory signals from the pixel signal intensity and from head motion in the patient head-feet direction. These signals were then compared with data acquired simultaneously from the pulse oximeter and the respiratory belt.

SUMMARY OF THE INVENTION

The invention provides for a medical apparatus, a computer program product, and a method in the independent claims. Embodiments are given in the dependent claims.

Embodiments may provide for a system that provides for an improved means of measuring a cardiac motion signal using a camera. Examples may do this by measuring a series of images and then tracking the motion of groups of pixels within the series of images. This may have an advantage over other approaches such as looking at pixel signal intensity because it does not rely on imaging a region of skin that is filling and draining with blood. Detecting small motions in groups of pixels allows the detection of small motions in the subject to cardiac motion. In the thorax this may be differentiated from the monitoring of chest motion:

Amplitude: amplitude of cardiac induced motion is at least one or two order of magnitude smaller. Hence, high resolution optical imaging (lens, sensor, light) may be possibly beneficial to capture that type of motion, and the tracking algorithm may possibly also be sensitive to very small motion (typically: sub-pixel) of small duration.

Frequency: frequency of cardiac induced motion is around 60-100 beats per minute, while respiration is between 10 and 20 cycles per minute. Hence, higher temporal resolution of the optical camera is required to capture the waveform. Measuring at a rate of 10 frames per second or higher may be useful in differentiating between breathing and cardiac motion in the thorax.

While it is well known that the chest is moving up and down due to breathing, the existence of small chest vibrations due the cardiac beat is not known. Experimental measurement of a cardiac motion signal using a series optical images of a subject's thorax are provided herein and compared to an ECG and a PPG signal. The usefulness of this cardiac motion signal is illustrated with gated MRI images of the same subject's heart that were acquired using the cardiac motion signal to gate the acquisition of the magnetic resonance imaging data.

In one aspect the invention provides for a medical apparatus comprising an optical imaging system configured for acquiring a series of optical images descriptive of cardiac motion of a subject. The cardiac motion of the subject may for example be cardiac activity-induced body motion. In different examples the type of cardiac motion recorded by the camera may be different. In some instances the optical imaging system may image a chest or thorax region or have its image diverted by motion of the chest. In other examples the optical imaging system may image surfaces which are moved or vibrated by blood flowing through an artery.

The medical apparatus comprises a memory for storing machine-executable instructions. The medical apparatus further comprises a processor for controlling the medical apparatus. Execution of the machine-executable instructions causes the processor to repeatedly acquire a series of images using the optical imaging system. The series of images are acquired at a rate of at least 10 FPS. Execution of the machine-executable instructions further cause the processor to repeatedly drive a cardiac motion signal from the series of images. The cardiac motion signal is derived by tracking motion of at least a group of pixels within the series of images. For example an algorithm could look for or identify edges or groups of pixels within the series of images and examine how they move on a small scale. For example the group of pixels or edge identified in the image may move by say one or several pixels within one cardiac cycle. This embodiment may be beneficial because it may enable determination of a cardiac motion signal without the need to place wires, electrodes or other sensors on the subject directly.

In another embodiment, execution of the machine-executable instructions further cause the processor to modify an acquisition of medical image data by a medical imaging system using the cardiac motion signal. The medical imaging system is configured for acquiring the medical image data from a subject within an imaging zone. This embodiment may be beneficial because it may more easily enable modification of the operating of the medical imaging system to account for the motion phase of the heart and/or the heart rate.

In another embodiment, execution of the machine-executable instructions further cause the processor to trigger a gated acquisition of medical image data by a medical imaging system using the cardiac motion signal. As used herein the term trigger a gated acquisition means to control when the medical imaging system acquires the medical image data using the cardiac motion signal. The medical imaging system is configured for acquiring the medical image data from a subject within an imaging zone. This embodiment may be beneficial because it may more easily enable cardiac phase result or gated medical images to be acquired that are either of the cardiac phase-dependent or are gated such that cardiac motion does not affect the images.

In another embodiment, the medical apparatus comprises the medical imaging system.

In another embodiment, the medical imaging system is a magnetic resonance imaging system. The memory further comprises pulse sequence commands for controlling the magnetic resonance imaging system to acquire the magnetic resonance data according to a cardiac gated magnetic resonance imaging protocol. A magnetic resonance imaging protocol as used herein encompasses a magnetic resonance imaging protocol that may be used to image the heart. In some examples, it may also include an area around the heart at a particular phase or group of cardiac motion phases. This embodiment may be beneficial because it may provide for an easy means of measuring a cardiac motion signal and gating it during magnetic resonance imaging without the need to place electrodes or sensors on a subject. Also monitoring the heart may provide benefits in directly measuring the cardiac motion more directly to the heart. In other instances such as when images are being processed in the brain different regions such as arteries in the neck can be targeted so that the cardiac motion signal is more representative of blood flow in the brain than when directly measured by an ECG or over the chest of the subject. In other applications parameters such as the echo time (TE) or pulse repetition time (TR) are adjusted to account for the value of the heart rate. There are some magnetic resonance imaging protocols that do not use cardiac trigger or gating, but are adjusted for individual heart rate measurements, In another embodiment, the magnetic resonance imaging protocol is any one of the following: an arterial spin labeling magnetic resonance imaging protocol, a diffusion imaging magnetic resonance imaging protocol, and a perfusion imaging magnetic resonance imaging protocol, a spin echo magnetic resonance imaging protocol, a fast spin echo magnetic resonance imaging protocol, a gradient echo magnetic resonance imaging protocol, an echo-planar magnetic resonance imaging protocol, and a steady-state free-precession magnetic resonance imaging protocol. For some of the above protocols the cardiac motion signal can be taken from a skin surface above the jugular artery of the subject.

In another embodiment, the medical imaging system is an X-ray machine.

In another embodiment, the medical imaging system is a CT or computed tomography machine.

In another embodiment, the medical imaging system is a positron emission tomography or PET machine.

In another embodiment, the medical imaging system is an single photon emission computed tomography or SPECT machine.

In another embodiment, the medical imaging system is a digital x-ray machine.

In another embodiment, the medical imaging system is an ultrasound machine.

In another embodiment, the gated acquisition is triggered according to any one of the following: a threshold of the cardiac motion signal, a derivative of the cardiac motion signal, and combinations thereof. This embodiment may be beneficial because it may provide for an accurate means of triggering the acquisition of magnetic resonance data according to a particular phase or motion of a subject's heart.

In another embodiment, the medical apparatus further comprises an illumination source to illuminate the surface within the imaging zone. For example, the illumination may be an infrared source or any visible light. In some instances, the optical imaging system may also be an infrared imaging system. The use of an illumination source may be beneficial because it may provide for a better operation of the optical imaging system and a more accurate determination of the cardiac motion signal.

In another embodiment, the optical imaging system is configured for imaging a surface of the subject.

This embodiment may be beneficial because the optical imaging system is imaging directly a surface of the subject. For example the camera could be looking at a chest region or it may be even imaging a skin surface of the subject such as the chest or a jugular vein. The surface of the subject may also include a garment or other object placed on the subject. For example in the case of a magnetic resonance imaging system a surface coil could be placed on the chest or thorax of a subject and the optical imaging system could be used to image the surface of the surface coil.

In some examples, the surface of the subject could have a textured surface or a surface coil could also have a texture printed on it that makes the detection of the motion of pixels easier when deriving the cardiac motion signal. For example a line art with an easily identifiable pattern or regular patterns could be identified in the series of images and allow more accurate determination of the cardiac motion signal.

In another embodiment, the optical imaging system is configured for imaging a reflective surface placed on a surface of a subject. For example, a small reflective surface or a mirror could be placed on the surface of the subject. Or, in other examples, a mirror or reflective surface could be placed on a surface coil which is then placed on the subject. The camera could for example be arranged such that it images a surface reflected by the reflective surface. This may be beneficial because motion of the subject due to the heart may cause an image reflected by the mirror to move sufficiently to be detected by the optical imaging system. Surprisingly when a subject heart beats the entire body has small vibrations due to actual motion of the heart or motion caused by blood pulsing through the arteries. Tests have shown that this works on essentially the entire body. In some places it works better than others. In particular the chest, throat, head, and feet are good places to measure vibrations in the body do the cardiac motion.

In another embodiment, in the case where the medical imaging system is a magnetic resonance imaging system the medical apparatus can further comprise a surface coil configured for placing on a surface of the subject. The surface coil may comprise a mirror. As mentioned above the surface of the subject may be freely selected, but the chest, throat, head, and feet are good places to measure vibrations in the body due to the cardiac motion.

In another embodiment, the optical imaging system is configured for being placed on a surface of the subject. In this embodiment the optical imaging system itself may be placed on the subject. The optical imaging system could then be focused so that it images any surface within its optical path. As the subject's surface moves a small amount due to cardiac motion the change in the orientation of the camera could for example be detected. In some examples when the optical imaging system is placed on the surface of the subject the camera may be directed towards an object which has a regular optical pattern or lines. This may facilitate the detection of the motion of the group of pixels and allow for a more accurate determination of the cardiac motion signal. As mentioned above the surface of the subject may be freely selected, but the chest, throat, head, and feet are good places to measure vibrations in the body due to the cardiac motion.

In another embodiment, execution of the machine-executable instructions further causes the processor to apply a low pass filter to the cardiac motion signal. This embodiment may be beneficial because it may enable to make the cardiac motion signal more robust.

In another embodiment, execution of the machine-executable instructions further cause the processor to apply a high pass filter to the cardiac motion signal. Again, this embodiment may enable the determination of the cardiac motion signal to be more accurate. In some examples, a combination of a high pass filter and a low pass filter may both be used. In this case the filter can be chosen such that both large and small motions, which are not related to the cardiac motion signal can be filtered out.

In another embodiment, the medical apparatus further comprises a respiration belt to acquire a chest expansion signal. Execution of the machine-executable instructions further cause the processor to acquire the chest expansion signal using the respiration belt. The triggered gated acquisition of the medical imaging data is further gated using the chest expansion signal. This embodiment may be beneficial because it may enable the medical imaging to be resolved not only on the cardiac motion but also as a function of the subject's breathing or chest position due to respiration.

In another embodiment, the medical apparatus further comprises a breathing sensor. Execution of the machine-executable instructions further cause the processor to acquire the breathing sensor data. The triggered gated acquisition of the medical imaging data is further gated using the breathing sensor. This embodiment may be beneficial because it may enable the medical imaging to be resolved not only on the cardiac motion but also as a function of the subject's breathing or chest position due to respiration. The breathing sensor may take different forms in different embodiments. For example the breathing sensor may be directly measured by an MRI system using for example a navigator, a camera, or even the same optical imaging system used to measure the cardiac motion signal. In another embodiment, execution of the machine-executable instructions further causes the processor to perform the triggered gated acquisition of the of the medical image data using the chest expansion signal.

In another embodiment, execution of the machine-executable instructions further causes the processor to subtract the breathing signal from the cardiac motion signal. For example there could be a known relation between the chest motion as measured by the respiration belt as to the position of the at least a group of pixels. The use of the respiration belt could then be used to subtract the effect of breathing and provide for a more accurate cardiac motion signal.

In another embodiment, the series of images is acquired at a rate of at least 15 FPS.

In another embodiment, the series of images is acquired at a rate of at least 20 FPS.

In another embodiment, the series of images is acquired at a rate of at least 25 FPS. Any of the above three frame rates may be beneficial because they may provide for improved resolution of the cardiac motion signal.

In another embodiment, the optical imaging system is configured for imaging motion on a surface on the subject with a spatial resolution of 1 mm or less. This may be beneficial because it may provide for an effective means of measuring the cardiac motion signal of the subject directly.

In another embodiment, the camera is mounted at least 0.5 m from the imaging zone of the medical imaging system. This may be beneficial because it may provide for an effective means of remotely measuring the cardiac motion signal of the subject.

In another embodiment the optical imaging system is any one of the following: at least one two-dimensional camera, at least one three-dimensional camera, and combinations thereof. For a three-dimensional camera, the depth value for a group of pixels may be monitored.

In another embodiment, the optical imaging system comprises a lens system comprising one or more lenses with a magnification factor of m. The optical imaging system further comprises an optical sensor array with a pixel size of r·s is a distance between an equivalent focal plane of the lens system and the optical sensor array. The optical imaging system is focused at a distance of L. $(r \cdot L)/(s \cdot m)$ is less than any one of the following: 2 mm, 1 mm, and 0.5 mm. This embodiment may be beneficial because it provides a means of specifying the optical imaging system which may be used for acquiring the series of images such that a cardiac motion signal can be derived.

In another embodiment, the optical imaging system is characterized by an equivalent focal length f. The optical imaging system further comprises an optical sensor array with a pixel size of r, wherein the optical imaging system is focused at a distance L. $(r \cdot L)/f$ is less than any one of the following: 2 mm, 1 mm, and 0.5 mm. This embodiment is an alternative to the previous embodiment and is formulated in terms of a pinhole model to describe mathematically the 3D to 2D projection characteristics of the optical imaging system. In this and the previous embodiment, a linear, equivalent approximation model of the whole optical system is used.

In another embodiment, the medical apparatus further comprises a display. Execution of the machine-executable instructions further causes the processor to display a heart rate derived from the cardiac motion signal and/or the cardiac motion signal on the display. This embodiment may be beneficial because it may provide for a convenient means of monitoring the cardiac motion signal.

In another embodiment, the group of pixels has a dimension of less than or equal to any one of the following: 80 by 80 pixels, 40 by 40 pixels, 20 by 20 pixels, and 10 by 10 pixels.

In another embodiment, the cardiac motion signal is derived by tracking the motion of a group of pixels within the series of images two dimensionally. This embodiment may be beneficial because it may provide a means of better detecting small motions on the surface of a subject caused by cardiac motion.

It is undersold herein that references to a group of pixels within the series of images may indicate that the group of pixels has dimension smaller than the each of the series of images. The group of pixels fits within each of the series of images or is smaller than each of the series of images.

In another embodiment, the cardiac motion signal is derived by calculating a two dimensional displacement of the group of pixels.

In another embodiment, the cardiac motion signal is derived by calculating an a scalar displacement of the group of pixels from an initial position. For example the position of the group of pixels within the series of images could be tracked two dimensionally. One of the series of images could be used to provide an initial position of the group of pixels. The overall two dimensional displacement could be used to calculate a vector displacement from the group of pixels to each of the series of images. The magnitude of the vector displacement could then be taken as the cardiac motion signal.

In another embodiment, the cardiac motion signal is derived by tracking the motion of multiple groups of pixels within the series of images two dimensionally. For example the cardiac motion signal could be an average motion signal derived from the two dimensional motion of the multiple groups of pixels within the series of images. As with the single group of pixels. One of the series of images could be used to provide an initial position for each of the multiple groups of pixels. The two dimensional displacement of each of the multiple groups could be used to calculate a vector displacement for each of the groups of pixels for each of the series of images. The magnitude of the vector displacement for each of the multiple groups could then be taken as the cardiac motion signal. In some instances, a weighting factor could be applied to the magnitude of the vector displacement for each of the multiple groups.

References to a group of pixels herein may be replaced with multiple groups of pixels.

In another aspect, the invention provides for a method of operating a medical apparatus. The medical apparatus comprises an optical imaging system configured for acquiring a series of optical images descriptive of cardiac motion of a subject. The method comprises repeatedly acquiring a series of images using the optical imaging system. The series of images are acquired at a rate of at least 10 FPS. The method further comprises repeatedly deriving a cardiac motion signal from the series of images. The cardiac motion signal is derived by tracking motion of at least a group of pixels within the series of images. The advantages of this embodiment have been previously given.

In another embodiment, the method further comprises focusing the camera on a surface of the subject. This embodiment may be beneficial because it may provide for a direct measurement of the cardiac motion signal from the surface. The surface of the subject may take different forms in different examples.

In another embodiment, the surface of the subject is any one of the following: a surface above the jugular artery such as a skin patch, a surface on the chest of the subject, and a surface above the heart of the subject.

In another aspect, the invention provides for a computer program product comprising machine-executable instructions for execution by a processor controlling a medical apparatus. The medical apparatus comprises an optical imaging system configured for acquiring a series of optical images descriptive of cardiac motion of a subject. Execution of the machine-executable instructions causes the processor to repeatedly acquire a series of images using the optical imaging system. The series of images are acquired at a rate of at least 10 FPS. Execution of the machine-executable instructions further causes the processor to repeatedly derive a cardiac motion signal from the series of images. The cardiac motion signal is derived by tracking motion of at least a group of pixels within the series of images.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage may be any volatile or non-volatile computer-readable storage medium.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the C programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, bluetooth connection, wireless local area network connection, TCP/IP connection, ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) display, Electroluminescent display (ELD), Plasma display panel (PDP), Liquid crystal display (LCD), Organic light-emitting diode display (OLED), a projector, and Head-mounted display.

Medical image data is defined herein as two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins using the antenna of a magnetic resonance apparatus during a magnetic resonance imaging scan. Magnetic resonance data is an example of medical image data. A Magnetic Resonance (MR) image is defined herein as being the reconstructed two or three dimensional visualization of anatomic data contained within the magnetic resonance imaging data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
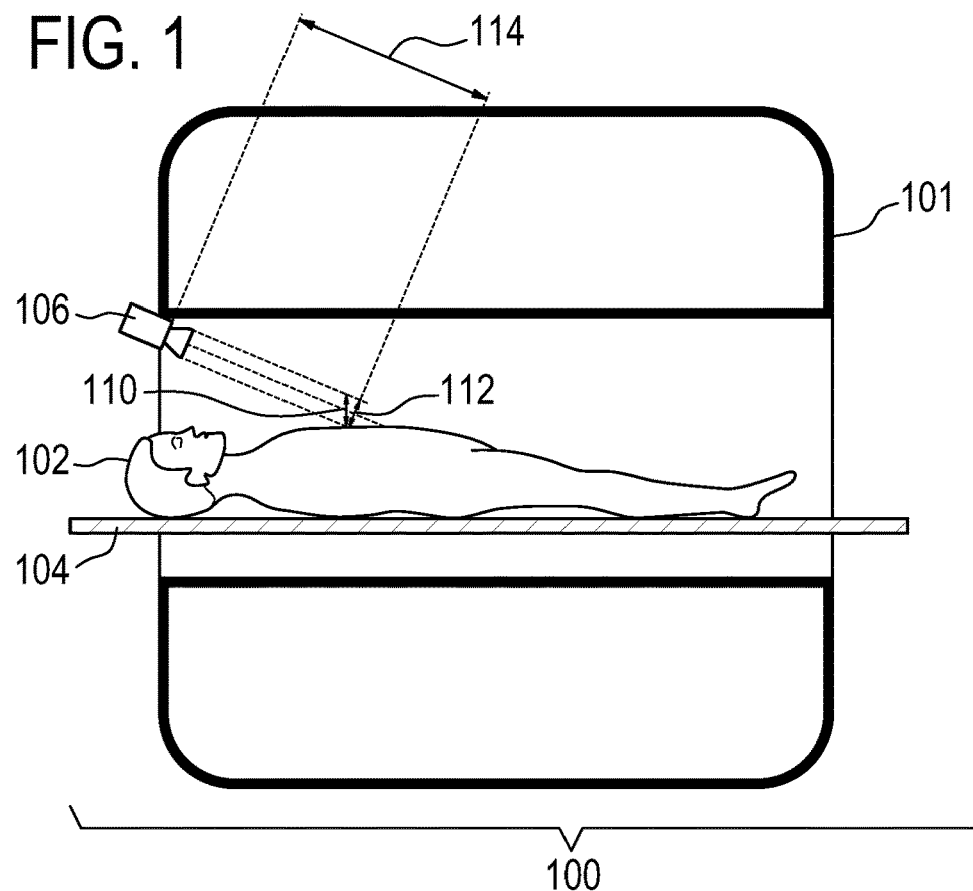
FIG. 1 illustrates an example of a medical instrument.

FIG. 1 shows an example of a medical instrument 100. The medical instrument 100 is shown as optionally containing a medical imaging system 101. There is a subject 102 reposing on a subject support 104. A camera 106 is focused on a chest region of the subject 102. The subject's chest moves in the direction 110 due to the subject's heart beating. This motion 110 can be imaged in the plane or the direction marked 112. The camera 106 is a distance 114 from the subject 102. As the subject's heart moves small differences in the image can be detected at the pixel level and can be used to derive a cardiac motion signal. The medical imaging system is intended to be representative and could for example be any one of the following: x-ray machine, a computer tomograghy (CT) machine, a positron emission tomography (PET) machine, a single photon emission computed tomography (SPECT) machine, a digital x-ray machine, and an ultrasound machine.

Figure 2:
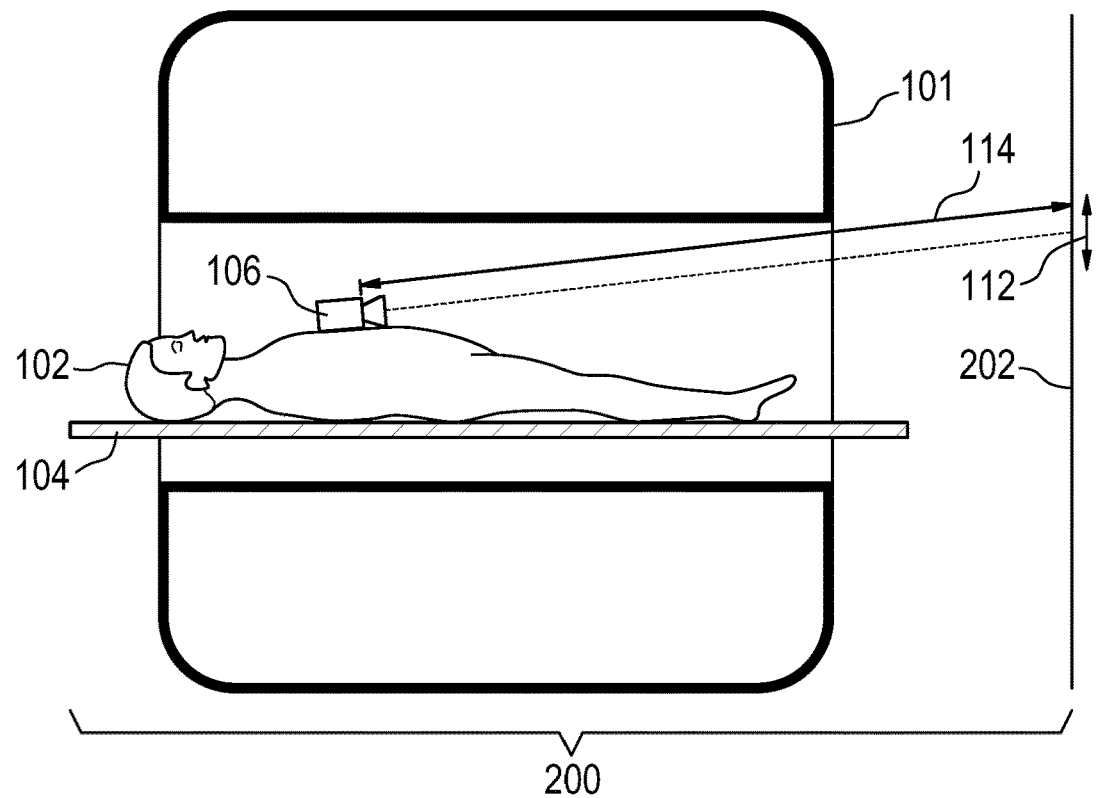
FIG. 2 illustrates a further example of a medical instrument.

FIG. 2 shows an alternate example of a medical instrument 200. In this example the camera 106 is shown as being placed on the chest of the subject 102. As the subject's heart beats the camera 106 will move a small amount. The camera 106 is focused on a different surface which in this subject is a wall 202. For example on the wall 202 there can be patterns or lines which can be easily detected by an edge detection or other image analysis algorithm. As the subject's 102 heart beats the camera 106 will move a small amount and small differences in the pixels in the series of images can be detected.

Figure 3:
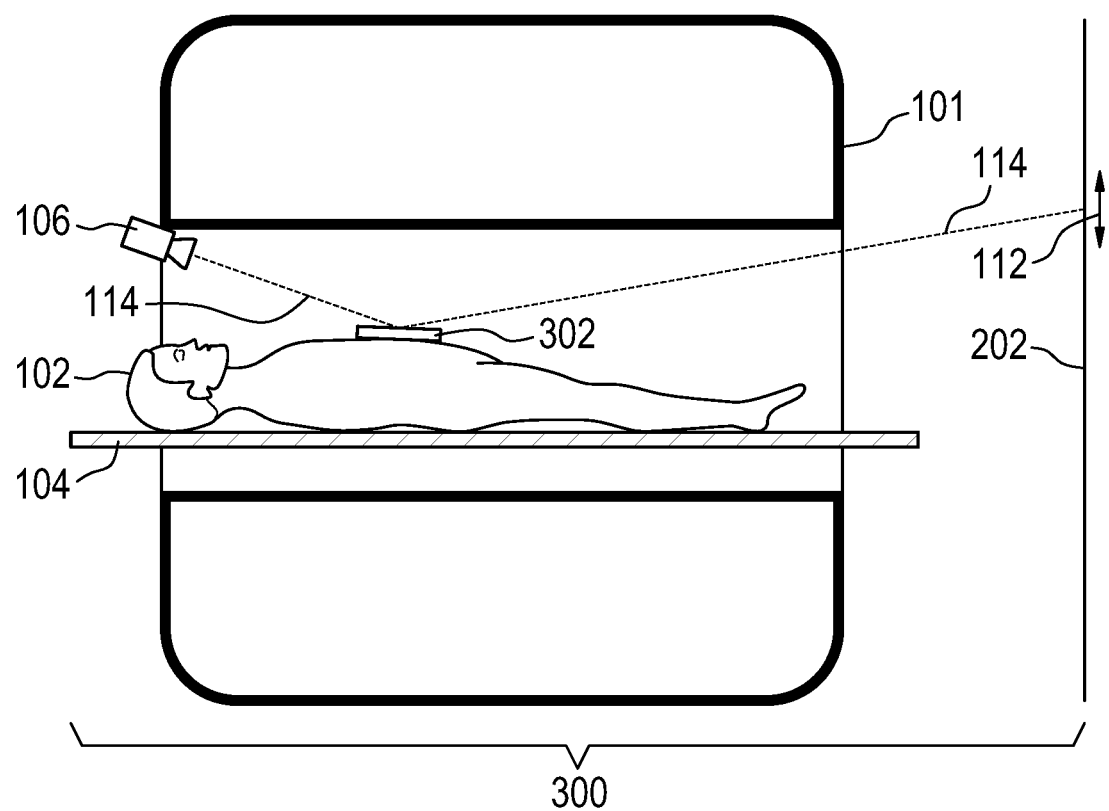
FIG. 3 illustrates a further example of a medical instrument.

FIG. 3 illustrates a further example of a medical instrument 300. In this example there is a reflective surface 302 placed on the chest of the subject 102. The camera 106 is then aimed at the reflective surface 302 such that a portion of the wall 202 is imaged. As the subject's heart beats small movements in the mirror 302 will cause the region imaged by the camera 106 to shift. Small differences in the pixels can be detected in a series of images to derive a cardiac motion signal. For example there can be patterns or lines placed on the wall 202 to facilitate this.

Figure 4:
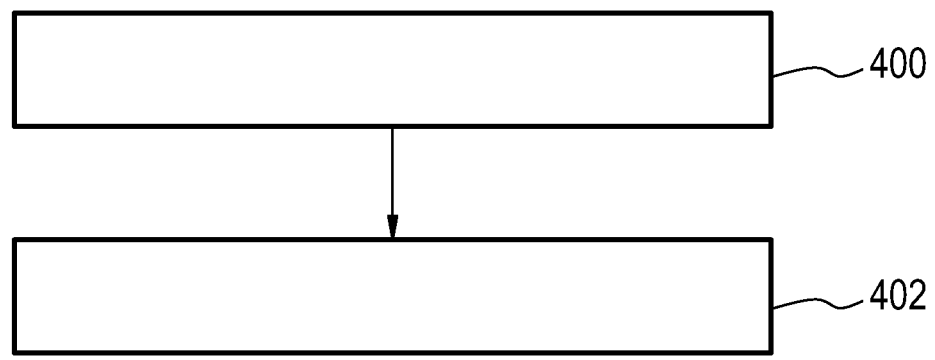
FIG. 4 shows a flow chart which illustrates an example of a method of operating the medical instruments in FIG. 1, 2, or 3.

FIG. 4 illustrates a method of operating any of the medical apparatuses illustrated in FIG. 1, 2 or 3. First in step 400 a series of images are acquired using the optical imaging system 106. Next in step 402 a cardiac motion signal is derived from the series of images. The cardiac motion signal is derived by tracking motion of at least a group of pixels within the series of images.

Figure 5:
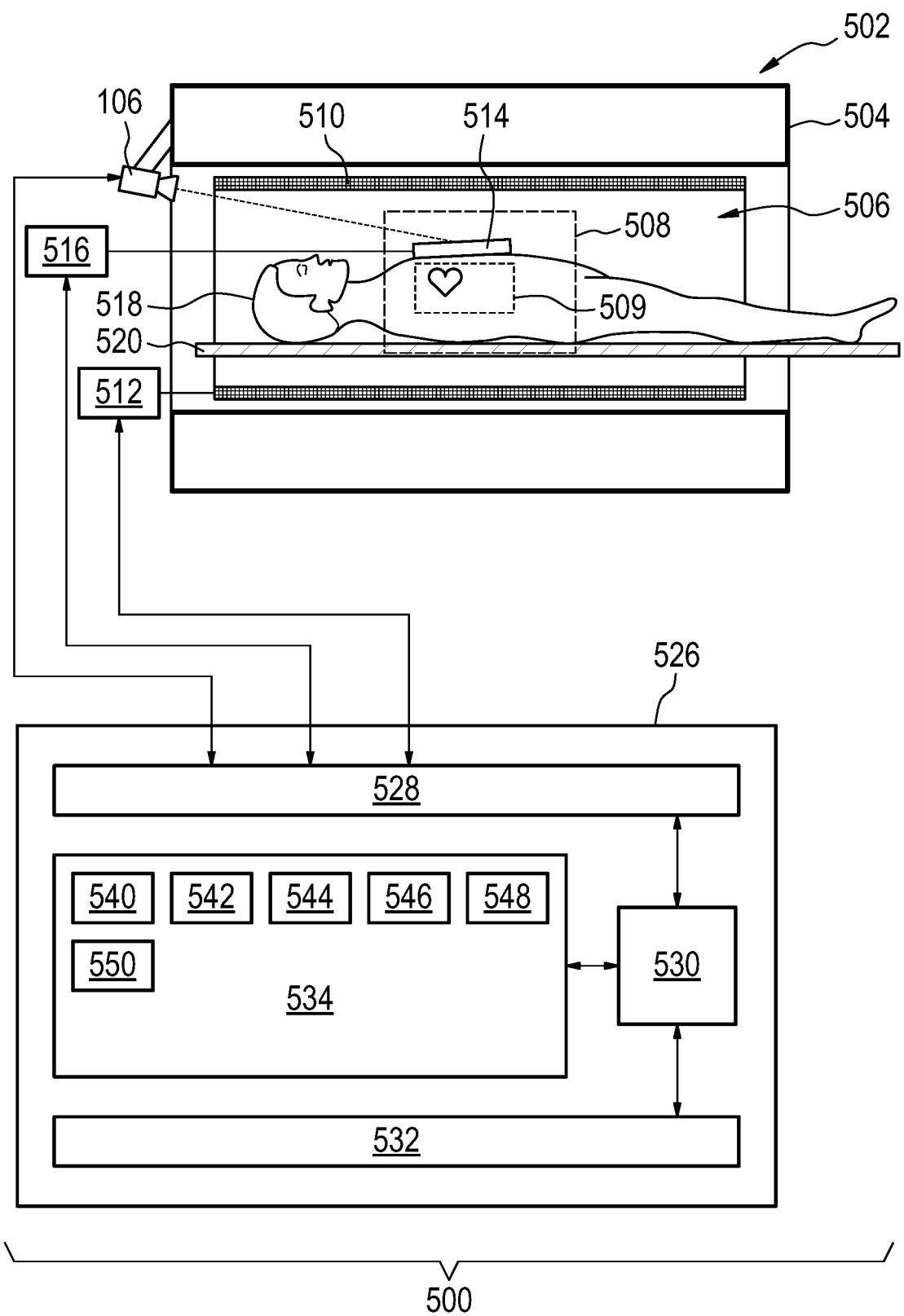
FIG. 5 illustrates a further example of a medical instrument.

FIG. 5 shows a further example of a medical instrument 500. In this example the medical instrument 500 comprises a magnetic resonance imaging system 502. The magnetic resonance imaging system 502 comprises a magnet 504. The magnet 504 is a superconducting cylindrical type magnet with a bore 506 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 506 of the cylindrical magnet 504 there is an imaging zone 108 where the magnetic field is strong and uniform enough to perform magnetic resonance imaging. A region of interest 509 is shown within the imaging zone 508. A subject 518 is shown as being supported by a subject support 520 such that at least a portion of the subject 518 is within the imaging zone 508 and the region of interest 509.

Within the bore 506 of the magnet there is also a set of magnetic field gradient coils 510 which is used for acquisition of magnetic resonance data to spatially encode magnetic spins within the imaging zone 508 of the magnet 504. The magnetic field gradient coils 510 connected to a magnetic field gradient coil power supply 512. The magnetic field gradient coils 510 are intended to be representative. Typically magnetic field gradient coils 510 contain three separate sets of coils for spatially encoding in three orthogonal spatial directions. A magnetic field gradient power supply supplies current to the magnetic field gradient coils. The current supplied to the magnetic field gradient coils 510 is controlled as a function of time and may be ramped or pulsed.

Adjacent to the imaging zone 508 is a radio-frequency coil or surface coil 514 for manipulating the orientations of magnetic spins within the imaging zone 508 and for receiving radio transmissions from spins also within the imaging zone 508. The radio frequency antenna may contain multiple coil elements. The radio frequency antenna may also be referred to as a channel or antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio frequency transceiver 516 are representative. The radio-frequency coil 514 is intended to also represent a dedicated transmit antenna and a dedicated receive antenna. Likewise the transceiver 516 may also represent a separate transmitter and receivers. The radio-frequency coil 514 may also have multiple receive/transmit elements and the radio frequency transceiver 516 may have multiple receive/transmit channels. For example if a parallel imaging technique such as SENSE is performed, the radio-frequency could 514 will have multiple coil elements.

In this example a camera 106 can be seen as being mounted on the flange of the magnet 504. A surface coil 514 on the subject's chest is imaged by the optical imaging system 106. As the subject's 518 heart beats the surface coil 514 will move up a small amount. In other examples, wherein there is no surface coil, the camera could image the motion of a skin patch or garment as it moves due to cardiac motion or cardiac induced motion.

The transceiver 516, the gradient controller 112, and camera 106 are shown as being connected to a hardware interface 528 of a computer system 526. The computer system further comprises a processor 530 that is in communication with the hardware system 528, a memory 534, and a user interface 532. The memory 534 may be any combination of memory which is accessible to the processor 530. This may include such things as main memory, cached memory, and also non-volatile memory such as flash RAM, hard drives, or other storage devices. In some examples the memory 530 may be considered to be a non-transitory computer-readable medium.

The computer memory 534 is shown as containing machine-executable instructions 540. The machine-executable instructions contain commands or instructions which enable the processor 530 to control the operation and function of the magnetic resonance imaging system 502. The computer memory 534 is shown as further containing pulse sequence commands 542. The pulse sequence commands 542 are either instructions or data which may be converted into instructions which enable the processor 530 to control the magnetic resonance imaging system 502 to acquire magnetic resonance data.

The computer memory 534 is shown as containing a series of images 544 acquired with the optical imaging system 106. The various images in the series of images 544 can be compared to identify groups of pixels that are moving to derive a cardiac motion signal 546 which is also shown as being stored in the memory 534. For example the method illustrated in FIG. 4, could be performed repeatedly to generate the cardiac motion signal 546 which can be used to trigger the acquisition of magnetic resonance data 548 using the pulse sequence commands 542. The magnetic resonance data 548 can then be reconstructed into a magnetic resonance image 550.

The monitoring of the cardiac activity during medical imaging examinations (MRI/CT/PET/ . . . ), and especially for triggering or gating during scan acquisition, has conventionally been done using sensors applied to the patient, e.g. ECG or PPG.

Examples may use an optical imaging system (for example a video camera) and with image processing to detect and track the subtle motion of the body parts (e.g. chest) that occurs as a consequence of the cardiac contraction or cycle. This is a new approach that may for example use intensity variations of the skin color used to measure cardiac pulse with a video camera.

Examples may contain one or more of the following features:
An optical imaging system (video camera) positioned such that motions of the target body part can be detected. An optical imaging system that can image the Infrared (IR) spectrum (IR light source and IR sensor) may be advantageous, but not mandatory. The motion of an object placed on e.g. the chest, such as a RF coil or surface coil for MRI, can be used as surrogate as well.
The optical path (distance between object and camera, optical zoom, sensor resolution, light conditions) can for example be designed such that motion amplitude of 0.1 mm or more can be detected and tracked with a speed of 10 or even possibly 20 frames per second or more.
A processing algorithm that extracts a cardiac motion signal from the video stream, with one or more of the following properties:
The predominant (e.g. anterior-posterior) component of the body surface motion is extracted
Motion not due to cardiac activity is suppressed, either using filtering techniques such as low-band frequency cut filters, or by measuring in parallel bulk motion and breathing motion and combining the obtained signals.
A triggering processing algorithm that detects the beginning of each cardiac cycle due to the particular shape of the extracted cardiac waveform in order to trigger or gate scan acquisition.

Examples may have one or more of the following advantages:
Workflow improvement: no need to place a sensor on the patient. No dedicated technical/medical expertise required, contrary to ECG.
Robust signal acquisition:
An electrocardiogram (ECG) signal is very often highly corrupted in MRI environment, especially at 3T, making it completely useless in these cases.
Quality of a photoplethysmogram (PPG) signal (SNR) is highly patient-dependent and can vanish over-time when peripheral circulation decreases, for example as a result of sustained pressure of the devices at the attachment location. It is also very sensitive to motion of the device.
Delays with respect to the true cardiac contraction are shorter and less patient-dependent than for PPG.

The monitoring of cardiac activity is necessary for many medical imaging applications, e.g. for gating or triggering, especially for cardiac scans. Cardiac motion is often measured by means of an ECG sensor using electrodes that are placed on the chest of the patient to record the cardiac electrical activity. A known technical alternative to the ECG sensor in MR applications is a PPG sensor that monitors the cardiac pulsation using a finger clip.

Examples may solve one or more of the following problems:
Known problems associated with the use of regular physiology sensors such as hardware reliability, cost, errors or inaccuracies due to wrong positioning of the device, hampered workflow, etc
ECG signal is very often highly corrupted in MRI environment, especially at 3T, making it completely useless in these cases.
Quality of PPG signal (SNR) is highly patient-dependent and can vanish over-time when peripheral circulation decreases, for example as a result of sustained pressure of the devices at the attachment location. It is also very sensitive to motion of the device.
Delays with respect to the true cardiac contraction are patient-depend and relatively long in PPG (in the order of a few 100 ms), which can lead to inaccurate triggering of the MR sequence
As opposed to other cardiac pulse monitoring approaches based on video camera, it is required to image a portion of the skin.

As previously mentioned examples may use a video camera and dedicated processing to detect and track the subtle motion of the body surface (e.g. chest) that occurs as a consequence of the cardiac contraction and the mechanical pressure wave in the body.

This is a different approach than previously known techniques based on skin intensity variations used to measure cardiac pulse with a video camera. The components of an example may include one or more of the following features:

A video camera positioned such that motions of the chest or other surface such as the throat can be detected. IR spectrum (IR light source and IR sensor) is of advantage, but not mandatory.

The optical path (distance between object and camera, optical zoom, sensor resolution, light conditions) may be designed such that motion amplitude of 0.1 mm or more can be detected and tracked with a speed, for example, of 20 frames per second or more.

A processing algorithm that extracts a cardiac motion signal from the video stream, with following properties:

Only the predominant (e.g. anterior-posterior) component of the body surface motion is extracted Motion not due to cardiac activity is suppressed, either using filtering techniques such as low-band frequency cut filters, or by measuring in parallel bulk motion and breathing motion and combining the obtained signals.

A triggering processing algorithm that detects the beginning of each cardiac cycle due to the particular shape of the cardiac waveform.

Figure 6:
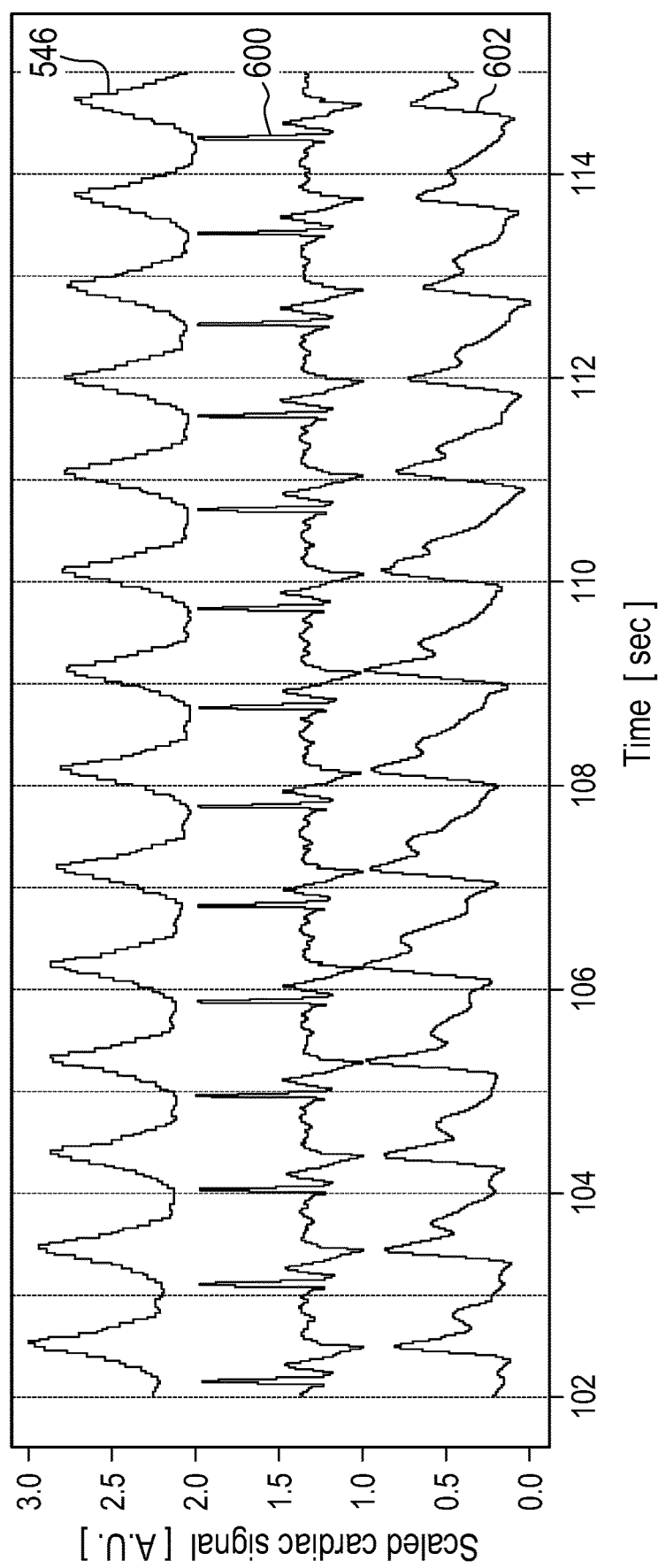
FIG. 6 compares a measured cardiac motion signal to an ECG signal and a PPG signal.

FIG. 6 shows an example of a cardiac motion signal 546 acquired using a setup similar to that shown in FIG. 5 with an ECG signal 600 and a PPG signal 602 plotted simultaneously. It can be seen in this FIG. that the cardiac motion signal 546 derived from the series of images 544 is comparable to both the ECG sensor 600 and the PPG sensor data 602.

Figure 7:
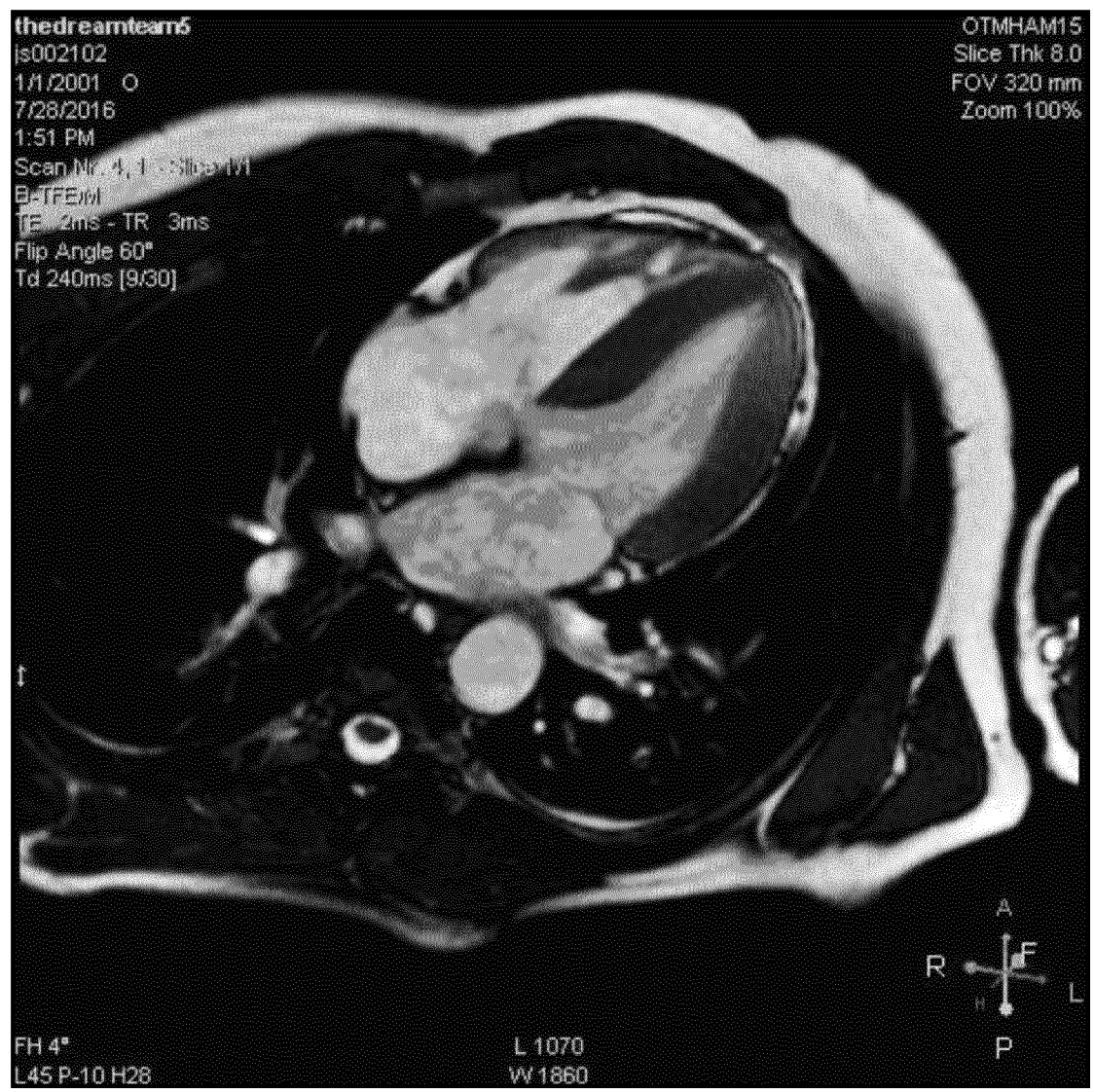
FIG. 7 shows an example of a cardiac magnetic resonance image gated with an ECG signal.
Figure 8:
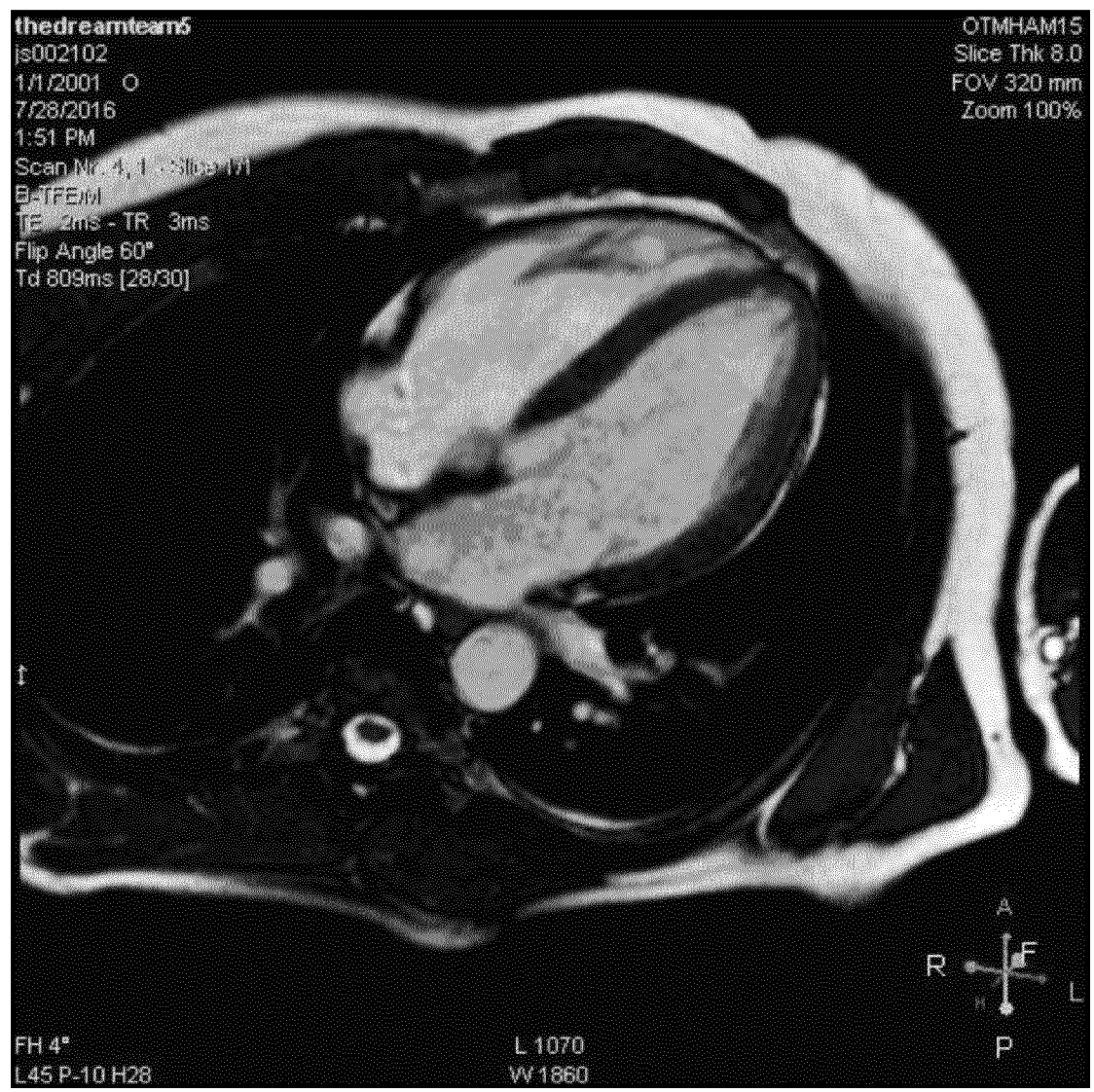
FIG. 8 shows a further example of a magnetic resonance image gated with the ECG signal.

FIGS. 7-10 are used to show a comparison between MRI gated with an ECG signal (FIGS. 7 and 8) and the cardiac motion signal 546 (FIGS. 9 and 10) such as was acquired using the system illustrated in FIG. 5. FIGS. 7 and 8 show the end-systolic (FIG. 7) and the end-diastolic (FIG. 8) long axis views of the heart obtained with ECG gating for magnetic resonance imaging.

Figure 9:
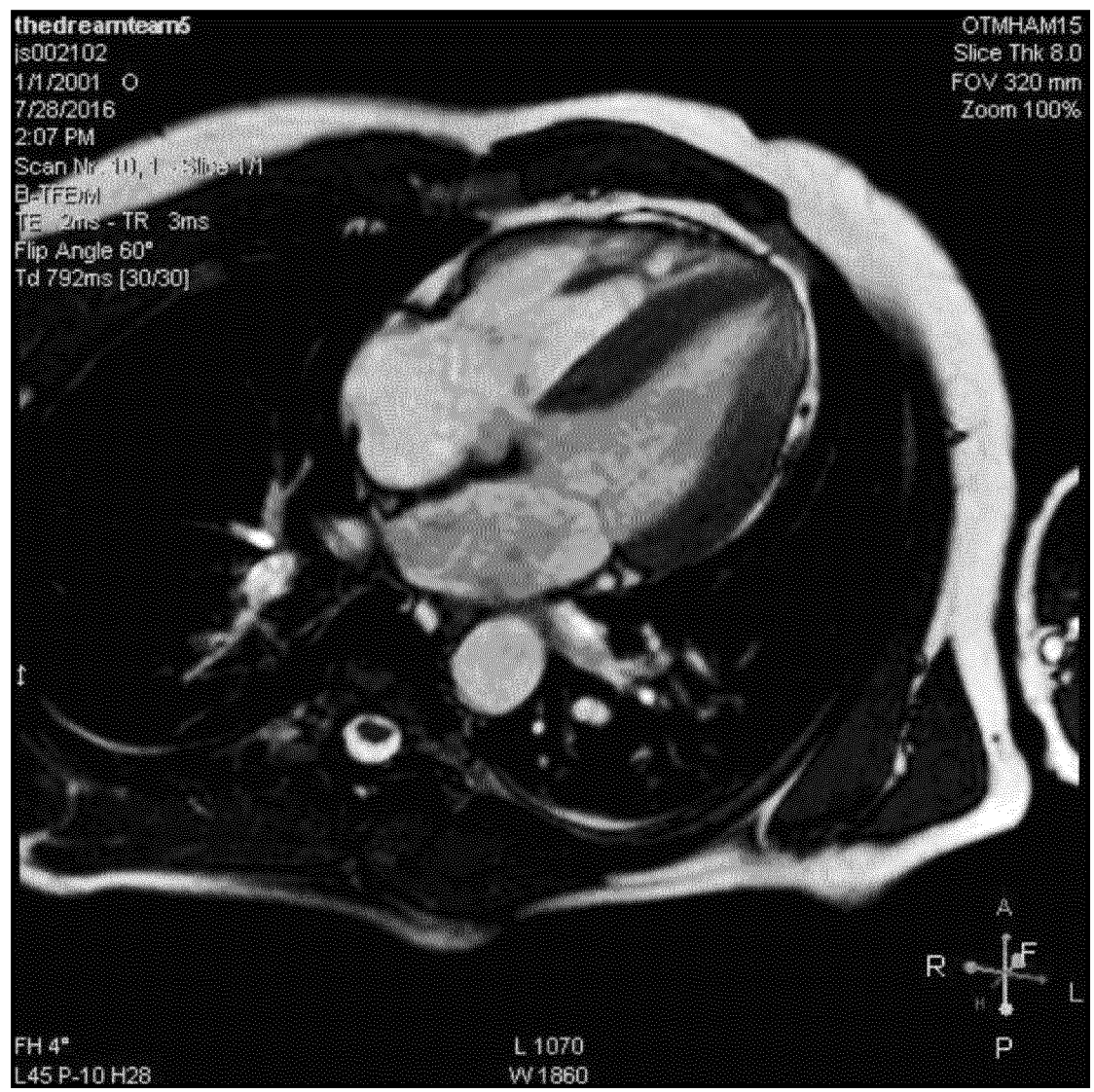
FIG. 9 shows an example of a magnetic resonance image gated with a cardiac motion signal.
Figure 10:
FIG. 10 shows a further example of a magnetic resonance image gated with the cardiac motion signal.

FIGS. 9 and 10 show the end-systolic (FIG. 9) and the end-diastolic (FIG. 10) long axis views of the heart obtained using the cardiac motion signal 546. FIG. 7 can be compared directly to FIG. 9 and FIG. 8 can be compared directly to FIG. 10. It can be seen that the use of the cardiac motion signal 546 produces gated magnetic resonance images of the heart which are comparable and of the same quality as those produced using an ECG signal 600. In FIGS. 7 to 10, the same cardiac phases were identified with both sensors and in both cases a similar depiction of the aortic valve was obtained, which indicates that the cardiac seismography sensor (cardiac motion sensor) leads to comparable gating performance as the ECG.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
101 medical imaging system
102 subject
104 subject support
106 optical imaging system
108 subject
110 motion caused by cardiac motion
112 image of motion
114 distance to lens
200 medical instrument
202 wall
300 medical instrument
302 reflective surface
400 acquire a series of images using the optical imaging system
402 derive a cardiac motion signal from the series of images
500 medical instrument
502 magnetic resonance imaging system
504 magnet
506 bore of magnet
508 imaging zone
509 region of interest
510 magnetic field gradient coils
512 magnetic field gradient coil power supply
514 radio-frequency coil
516 transceiver
518 subject
520 subject support
526 computer system
528 hardware interface
530 processor
532 user interface
534 computer memory
540 machine executable instructions
542 pulse sequence commands
544 series of images
546 cardiac motion signal
548 magnetic resonance data
550 magnetic resonance image
600 ECG signal
602 PPG signal

The invention claimed is:

1. A medical apparatus comprising:
 a medical imaging system;
 a two-dimensional camera disposed on or within the medical imaging system and configured for acquiring a series of optical images descriptive of cardiac motion of a subject, wherein the two-dimensional camera is configured for being placed on a surface of the subject;
 a non-transitory memory for storing machine executable instructions;

a processor for controlling the medical apparatus, wherein execution of the machine executable instructions causes the processor to repeatedly:
  acquire a series of images using the two-dimensional camera, wherein the series of images are acquired at a rate of at least 10 frames per second; and
  derive a cardiac motion signal from the series of images by detecting an edge or group of pixels within the series of images and tracking movement of the edge or group of pixels in the series of images two-dimensionally and extracting an anterior-posterior component of a body surface motion of the subject.

2. The medical apparatus of claim 1, wherein execution of the machine executable instructions further causes the processor to modify acquisition of medical image data by the medical imaging system using the cardiac motion signal, and wherein the medical imaging system is configured for acquiring the medical image data from the subject within a imaging zone.

3. The medical apparatus of claim 2, wherein the medical imaging system is a magnetic resonance imaging system, wherein the memory further contains pulse sequence commands for controlling the magnetic resonance imaging system to acquire the magnetic resonance data according to a magnetic resonance imaging protocol.

4. The medical apparatus of claim 3, wherein the magnetic resonance imaging protocol is any one of the following: an arterial spin labeling magnetic resonance imaging protocol, a diffusion imaging magnetic resonance imaging protocol, and a perfusion imaging magnetic resonance imaging protocol, a spin echo magnetic resonance imaging protocol, a fast spin echo magnetic resonance imaging protocol, a gradient echo magnetic resonance imaging protocol, an echo-planar magnetic resonance imaging protocol, and a steady-state free-precession magnetic resonance imaging protocol.

5. The medical apparatus of claim 2, wherein the medical imaging system comprises one of an x-ray machine, a CT machine, a PET machine, a SPECT, a digital x-ray machine, and an ultrasound machine.

6. The medical apparatus of claim 2, wherein the acquisition is triggered according to any one of the following: a threshold of the cardiac motion signal, a derivative of the cardiac motion signal, and combinations thereof.

7. The medical apparatus of claim 1, wherein the two-dimensional camera is configured for imaging a mirror placed on a surface of a subject.

8. The medical apparatus of claim 1, wherein the series of images is any one of the following: acquired at a rate of at least 15 frames per second, acquired at a rate of at least 20 frames per second, and acquired at a rate of at least 25 frames per second.

9. The medical apparatus of claim 1, wherein the two-dimensional camera comprises a lens system with an equivalent magnification factor of m, wherein the two-dimensional camera further comprises an optical sensor array with a pixel size of r, wherein s is a distance between an equivalent focal plane of the lens system and the optical sensor array, wherein the two-dimensional camera is focused at a distance L, wherein $(r \cdot L)/(s \cdot m)$ is less than any one of the following: 2 mm, 1 mm, and 0.5 mm.

10. The medical apparatus of claim 1, wherein the medical apparatus further comprises a display, wherein execution of the machine executable instructions further causes the processor to display a heart rate derived from the cardiac motion signal and/or the cardiac motion signal on the display.

11. The medical apparatus of claim 1, wherein the cardiac motion signal is derived by tracking the motion of at least a group of pixels within the series of images acquired by the two-dimensional camera two dimensionally.

12. The medical apparatus of claim 1, wherein the detecting of the edge or group of pixels within the series of images includes detecting intensity variations of skin color.

13. The medical apparatus of claim 1, wherein the cardiac motion signal is derived by calculating a two-dimensional displacement of a group of pixels within the series of images and tracking the two-dimensional displacement of the group of pixels in the series of images two-dimensionally and extracting an anterior-posterior component of a body surface motion of the subject.

14. A method of operating a medical apparatus, wherein the medical apparatus comprises an optical imaging system, the method comprises:
  acquiring, using a two-dimensional camera configured for being placed on a surface of a subject, a series of images descriptive of cardiac motion of the subject being imaged by a medical imaging system using an optical imaging system that is attached to a bore of the medical imaging system or to an exterior of the medical imaging system, wherein the series of images are acquired at a rate of at least 10 frames per second;
  deriving a cardiac motion signal indicative of the cardiac motion of the subject from the series of images by detecting an edge within the series of images and tracking movement of the edge in the series of images and extracting an anterior-posterior component of a body surface motion of the subject; and
  repeatedly performing the acquiring and the deriving to obtain the cardiac motion signal over time.

15. The method of claim 14, wherein the method further comprises focusing the optical imaging system on a surface of the subject, wherein the surface is any one of the following: a surface above the jugular artery, a surface on the chest of the subject, and a surface above the heart of the subject.

16. The method of claim 14, wherein the optical imaging system is attached to a bore of the medical imaging system.

17. The method of claim 14, wherein the optical imaging system is attached to an exterior of the medical imaging system.

18. A computer program product comprising a non-transitory computer readable medium configured to store machine executable instructions for execution by a processor controlling a medical apparatus, wherein the medical apparatus comprises an optical imaging system disposed on a patient disposed within a medical imaging system and configured for acquiring a series of optical images descriptive of cardiac motion of a subject, wherein execution of the machine executable instructions causes the processor to repeatedly:
  acquire a series of images of at least a chest of the subject using the optical imaging system, wherein the series of images are acquired at a rate of at least 10 frames per second; and
  derive a cardiac motion signal from the series of images, wherein the cardiac motion signal is derived by tracking motion of an edge or group of pixels within the series of images, wherein tracking is performed by extracting an anterior-posterior component of a body surface motion of the subject;
  wherein the tracking of the movement of the edge or group of pixels in the series of images does not include tracking pixel signal intensity variations caused by a region of skin filling and draining with blood.

* * * * *